United States Patent [19]

Konno et al.

[11] 4,298,740
[45] Nov. 3, 1981

[54] PROCESS FOR THE PRODUCTION OF THIOLCARBAMATE COMPOUNDS

[75] Inventors: Kazuhiko Konno; Atsushi Goh; Kiyoshi Sugaya, all of Ami, Japan

[73] Assignee: Mitsubishi Petrochemical Co., Ltd., Japan

[21] Appl. No.: 137,005

[22] Filed: Apr. 3, 1980

[30] Foreign Application Priority Data

Apr. 10, 1979 [JP] Japan .................................. 54-42576

[51] Int. Cl.$^3$ .................. C07D 211/06; C07D 207/24; C07D 209/32; C07C 155/02
[52] U.S. Cl. ............................ 546/226; 260/455 A; 260/239 E; 260/239 BF; 546/189; 546/225; 260/326.4; 260/239 A
[58] Field of Search ........ 260/455 A, 239 E, 239 AR, 260/239 BF, 326.4; 546/189, 225, 226

[56] References Cited

U.S. PATENT DOCUMENTS 3,897,492  7/1975  Tilles et al. ..................... 260/455 A
4,086,226  4/1978  Gozzo et al. ................... 260/455 A

FOREIGN PATENT DOCUMENTS 47-79985  8/1972  Japan .............................. 260/455 A
51-98331  8/1976  Japan .............................. 260/455 A

OTHER PUBLICATIONS

Noller, Textbook of Organic Chemistry, 2nd Ed., W. B. Saunders Company, Philadelphia, 1958.

Primary Examiner—Henry R. Jiles
Assistant Examiner—Robert C. Whittenbaugh
Attorney, Agent, or Firm—Wenderoth, Lind & Ponack

[57] ABSTRACT

In the process for the production of a thiolcarbamate compound of the formula

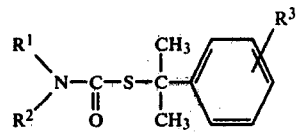

wherein $R^1$ and $R^2$ are as defined in claim, comprising reacting a tertiary halogen compound of the formula

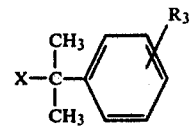

wherein X and $R^3$ are as defined in claim, with a thiolcarbamic acid salt of the formula

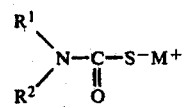

wherein M represents a member selected from the group consisting of the alkali metals, ammonium group and immonium group, in an aqueous reaction medium, in the presence of a strong base; the improvement wherein the reaction is carried out under conditions in which the reaction system is adjusted to a pH ranging from about 9 to about 13.

7 Claims, No Drawings

PROCESS FOR THE PRODUCTION OF THIOLCARBAMATE COMPOUNDS

This invention relates to an improved process for producing the thiolcarbamate compounds, which in view of their possession of a herbicidal activity are not only in themselves useful as herbicides but also useful as intermediates for the preparation of herbicidal preparations and other derivatives. More particularly, the invention relates to an improved process for the production of the thiolcarbamate compounds smoothly and in good yield from a tertiary halogen compound in which a nucleophilic subtitution reaction is not readily induced and an nucleophilic reagent, especially a thiolcarbamic acid salt, with good reaction reproducibility and advantageously from the operational standpoint.

More specifically, the invention relates to a process for producing a thiolcarbamate compounds of the formula

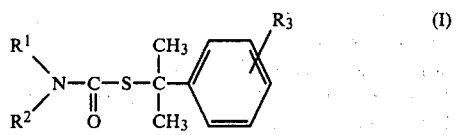

wherein $R^1$ and $R^2$, which may be the same or different, each represent a member selected from the group consisting of hydrogen, alkyl groups and alkenyl groups, and $R^3$ represents a member selected from the group consisting of hydrogen, halogen, nitro, alkyl groups and alkoxy groups, and in which $R^1$ and $R^2$ taken together with N in the formula which may form a hetero ring of the formula

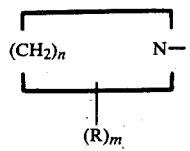

where R is hydrogen, m is an integer from 1 to 2, and n is an integer from 2 to 6, said process comprising reacting a tertiary halogen compound of the formula

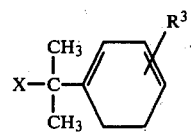

wherein X represents halogen, and $R^3$ is as defined above, with a thiolcarbamic acid salt of the formula

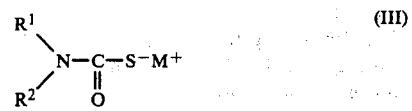

wherein M represents a member selected from the group consisting of the alkali metals, ammonium groups and immonium groups, in an aqueous reaction medium in the presence of a strong base; characterized in that the reaction is carried out under conditions in which the pH of the reaction system is adjusted to from about 9 to about 13.

The thiolcarbamate compounds of the foregoing formula (I), especially the α,α-dimethylbenzylthiolcarbamate compounds, include many compounds having a herbicidal activity. For example, the herbicidal activities of these compounds are disclosed in say Japanese Laid-Open Patent Publications Nos. 35530/74 and 98331/76.

A number of suggestions have been made in the past in regard to the preparation of the compounds of formula (I), but in none of the suggestions has it been possible to obtain the compounds of formula (I) smoothly and in satisfactory yields and moreover with good reaction reproducibility and advantageously from the operational standpoint. Thus, there has been a hope that a commercially satisfactory improved process would be developed.

It was an especially difficult matter to carry out smoothly the reaction of a tertiary halogen compound of the foregoing formula (II) and a thiolcarbamic acid salt of the foregoing formula (III). For instance, when an attempt is made to carry out a nucleophilic substitution reaction of the compounds of formulas (II) and (III) in water or an aqueous medium such as a water-containing solvent, the desired reaction is not induced smoothly but instead solvolysis and an elimination reaction of hydrogen halide become the principal reactions, with the consequence that there is hardly any formation of the intended condensation reaction product. The principal products formed are the benzyl alcohol derivatives (IV) and the α-methylstyrene derivatives (V) of the following general formulas:

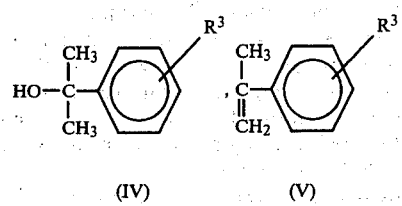

in which two formulas $R^3$ is as defined hereinbefore. Only a small quantity of the intended thiolcarbamate compounds of formula (I) is formed.

On the other hand, the aforementioned Japanese Laid-Open Patent Publication No. 98331/76 discloses in preparating a herbicidally active component that the α,α-dimethylbenzylthiolcarbamate compounds, which are includable in the foregoing formula (I), can be produced by reacting a cyclic amine, an alkali, carbonyl sulfide and a α,α-dimethyl benzyl halide in an inert medium, preferably water, an alcohol or a ketone in accordance with the following reaction equation

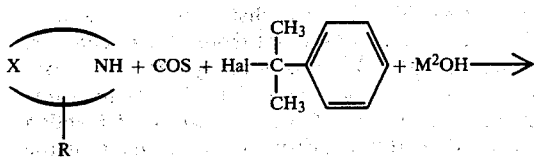

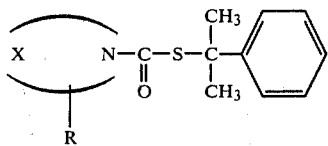

wherein X represents $-(CH_2)_n$ where n is an integer from 4 to 6 or $-CH_2-CH_2-O-CH_2-CH_2-$, R represents either hydrogen or a lower alkyl group, $M^2$ is an alkali metal atom or ammonium group, and Hal is halogen.

In the foregoing proposal there are shown two examples of preparing the α,α-dimethylbenzylthiocarbamate compounds in accordance with the above reaction equation. In one example 4.46 g (0.045 mole) of hexamethyleneimine and 1.50 g (0.0375 mole) of sodium hydroxide are dissolved in 8.5 ml of water and, while cooling the solution with water, 3.60 g (0.06 mole) of carbonyl sulfide is passed through, after which 4.64 g (0.03 mole) of α,α-dimethylbenzyl chloride is added. The mixture is then reacted for one hour while cooling it with water and then for a further 4 hours at 40°–50° C. to yield 5.6 g of crude N-(α,α-dimethylbenzylthio-carbonyl)hexamethyleneimine followed by purification by column chromatography to give 4.2 g (a yield of about 40 mole% based on thiolcarbamic acid salt) of the intended product. In another example 3.0 g (0.030 mole) of 2-methylpiperidine and 1.44 g (0.036 mole) of sodium hydroxide are dissolved in 8.5 ml of water and, while cooling the solution with ice, 2.70 g (0.045 mole) of carbonyl sulfide is passed through, after which 4.65 g (0.03 mole) of α,α-dimethylbenzyl chloride and 5 ml of acetone are added. The mixture is then reacted under ice cooling for one hour and then for a further 4 hours at 40°–50° C. to give 3.50 g (a yield of about 33.4 mole% based on thiolcarbic acid salt) of crude N-(α,α-dimethylbenzylthiocarbonyl)-2-methylpyridine.

The present inventors (one of the co-inventors of the aforementioned proposal is a co-inventor of this invention) have been carrying out researches with the view of overcoming the unsatisfactory yield of the intended compound in the foregoing proposal, i.e., a low yield of about 40 mole %, or even less.

As a consequence, it was found after repeated testing of the process disclosed in the foregoing proposal that not only was there the drawback that the yield of the process was low, but there was also the shortcoming as regards the reproducibility of the reaction. Hence, it was found that both the yield and the reaction reroducibility had to be improved for practicing the process on a commercial scale.

We engaged in extensive researches with the view of determining the factors which bring about these disadvantages and shortcomings. As a result of these researches, we found that the principal factor involved in improving the foregoing disadvantages and shortcomings was the pH of the reaction system wherein the reaction between the compound of formula (II) and the compound of formula (III) was carried out, a factor that had been completely overlooked in the above proposal.

We found by our researches that in the two examples given in the foregoing proposal there was a decline in both instance in the pH value of the system as the reaction proceeded, with the consequence that the pH value that had been about 12–13 at the outset of the reaction had declined to the neighborhood of about 8 in the latter stages of the reaction. Furthermore, the decline was not uniform. It was thus found that the unsatisfactory results as regards the yield and the reaction reproducibility were principally due to these factors.

As a consequence of having furthered our researches on the basis of this new finding, we discovered that by reacting a tertiary halogen compound of formula (II) with a thiolcarbamic acid salt of formula (III), which had been previously formed, and in carrying out the reaction by adjusting the pH of the reaction system to range from about 9 to about 13, preferably about 9.5 to about 12.5, and more preferably about 10 to about 12, it was possible to produce high purity thiolcarbamate compounds of formula (I) smoothly and advantageously from the operational standpoint in markedly improved yields reaching as high as 85 mole% as well as with superi- or reaction reproducibility.

It was further found that the compounds of formulas (IV) and (V) that are obtainable as by-products can be readily converted to the compound of formula (II) by treating them with a halogenating agent, for example, a hydrogen halide gas or a hydrohalogenic acid and that thus the commercial practice of the improved process of the present invention could be carried out still more advantageously by the use of the regenerated formula (II) compounds in the reaction.

According to our studies, it is believed that the strong base, preferably sodium hydroxide, potassium hydroxide or ammonia that is added and caused to be present in the reaction system during the reaction between the formula (II) tertiary halogen compound and the formula (III) thiolcarbamic acid salt has the effects of checking the objectionable hydrolysis of the formula (II) tertiary halogen compund and preventing the objectionable decomposition of the formula (III) thiolcarbamic acid salt as well as the effect of promoting the formation of the intended compounds of formula (I), these effects being manifested advantageously with good reproducibility in the pH zone specified above. However, it was found that if, as in the prior proposal described above, the pH value departs to below the zone specified hereinabove, the desired improvement could not be achieved. Hence, it was found that the reaction has to be carried out under conditions in which the pH value of the reaction system has been adjusted to come within the aforesaid pH zone.

That the reaction between the formula (II) tertiary halogen compound and the formula (III) compound could be advantageously promoted by a simple procedure of merely adjusting the pH and that by doing thus the formula (I) thiolcarbamate compounds could be produced smoothly and advantageously from the operational standpoint in good yield and with good reaction reproducibility was indeed unexpected.

It is therefore an object of the present invention to provide an improved process for producing commercially advantageously the thiolcarbamate compounds of formula (I).

The foregoing object and many other objects and advantages will become still more apparent from the following description.

In practicing the process of the instant invention the reaction is carried out either in water or an aqueous reaction medium comprising a mixture of water and an organic solvent that is miscible therewith in the presence of a strong base, preferably sodium hydroxide, potassium hydroxide and/or ammonia. The use of NaOH is especially preferred. According to the invention process it is necessary that the reaction be carried out under conditions in which the pH value of the reaction system has been adjusted to come within the range of about 10 to about 12, preferably about 9.5 to about 12.5, more preferably about 10 to about 12, and particularly about 10 to about 11. The reaction should be carried out under conditions in which the pH value has been adjusted to come within the zones indicated above from the outset of the reaction to its termination, though a departure of the pH value from the foregoing zones temporarily for a short period of time is permissible.

For example, even though the reaction is initiated with a pH coming within the foregoing zone, if, as in the prior proposal, the reaction is carred out without adjusting the pH, i.e., the reaction is carried out for a substantial period of time outside the foregoing zone, it becomes impossible to achieve the aforementioned improvements of the present invention.

The mode of carrying out the reaction under conditions in which the pH value of the reaction system is adjusted to about 9 to about 13 can be modified in various ways. For example, the reaction can be initiated within a pH zone of the foregoing pH zones, after which the reaction can be carried out with an addition to the system in advance of a strong base in an amount sufficient to ensure that the pH value does not decline to below the lowest of said pH zones. Alternatively, the reaction can be carried out within the aforesaid pH zones by adding additional amounts of the strong base to the reaction system incrementally or continuously as the reaction proceeds or the pH declines. Detter results are had by employment of the latter mode. The amount of strong base to be added can be suitably chosen so as to adjust the pH to come within the foregoing pH zones. For example, a preferred range is about 0.1 to about 1.6 moles, and a still more preferred range is about 0.5 to about 1.2 moles, per mole of the compound of formula (II).

While the molar ratio in which the formula (II) tertiary halogen compound and the formula (III) thiolcarbamic acid salt is reacted can also be suitably chosen, the use of the formula (II) compound in an amount of about 0.8 to about 6 equivalents, and preferably about 2 to about 4 equivalents of the formula (III) compound, will do. The formula (II) compound is preferably used in such an amount that it becomes excessive relative to the formula (III) compound at the time of the completion of the reaction, but if it becomes to excessive, there is an increased formation of the formula (IV) and/or formula (V) by-products. Hence, it is recommended that the formula (II) compound be used in the amounts indicated above.

The reaction is carried out in either water or a mixture of water and an organic solvent miscible therewith. As the solvents to be used in the latter case, there can be mentioned as examples the ethers such as diethyl ether, dioxane, tetrahydrofuran or the like, the ketones such as acetone, methyl ethyl ketone or the like, the lower aliphatic nitriles such as acetonitrile, propionitrile or the like, and the lower aliphatic amides such as N,N-dimethylformamide or the like.

As the reaction temperature, preferably used is one from about 0° to about 100° C., and more preferably from about 30° to about 70° C. The reaction time can be suitably chosen, but by way of example one from about 0.5 hour to about 5 hours will do.

After completion of the reaction, the separation to say the aqueous reaction medium phase and the oil phase (the phase containing the intended formula (I) product and the formula (IV) and formula (V) by-products) is separated by such means as the liquid separating technique and the intended formula (I) product and the formula (IV) and formula (V) by-products are separated and collected say by distilling the oil phase directly, converting the by-product (IV) to compound (V) by the hereinafter-described method followed by submitting the latter to distillation or recrystallization.

In carrying out the process of this invention the compounds of formula (IV) and (V) can be readily transformed in good yield to the compounds of formula (II) by treating them with a hydrogen halide gas or a hydrohalogenic acid. It is thus convenient in commercial practice to convert these by-product compounds to the compounds of formula (II) and reuse them in the reaction with the compound of formula (III).

The conversion of the compounds of formulas (IV) and (V) to the compounds of formula (II) can be carried out say in the following manner. A mixture of the compounds of formulas (IV) and (V) or the individual components are reacted with a halogenating agent in the absence of a solvent or in the presence of an inert solvent. In view of say the ease of the aftertreatment, a system in which a solvent is absent is to be preferred. The halogenating agent can be used in any amount that is at least equimolar to the amount of the compounds of formulas (IV) and (V), but usually the amount used is about 2-5 moles. While a reaction temperature ranging from 0° to 50° C. can be used, a reaction temperature of 20°-30° C. is most suitable when such factors as the reaction speed and the stability of the compound of formula (II) are considered. There is no particular need to purify the resulting product. For example, when a hydrohalogenic acid used, if the product is separated into an oil phase and an aqueous phase by the liquid separating technique, the compound of formula (II) can be obtained in sufficient purity as to cause no trouble in the following condensation reaction.

It thus becomes possible to produce, as described hereinbefore, smoothly and advantageously from the operational standpoint the thiolcarbamate compounds of formula (I) from the tertiary halogen compounds and the thiolcarbamic acid salts of formula (II) in good yield and with satisfactory reaction reproducibility.

In the foregoing formulas (I)–(III) examples of the $R^1$ and $R^2$ include, in addition to hydrogen, such $C_1$–$C_8$ alkyl groups as methyl, ethyl, n-propyl, i-propyl, n-butyl, sec-butyl, n-amyl, n-hexyl, n-heptyl and n-octyl groups, and such $C_3$–$C_8$ alkenyl groups as allyl, 2-butenyl, 3-butenyl, 2-pentenyl, 2-hexenyl, 2-heptenyl and 2-octenyl groups. On the other hand, examples of the halogen of $R^3$ include fluorine, chlorine, bromine and iodine, and as the $C_1$–$C_8$ alkyl groups of $R^3$ there can be mentioned say methyl, ethyl, n-propyl, i-propyl, n-butyl, sec-butyl, n-amyl, n-hexyl, n-heptyl and n-octyl groups. As the alkoxy groups, mention can be made of such $C_1$–$C_5$ alkoxy groups as methoxy, ethoxy, n-propoxy, i-propoxy, n-butoxy and m-amyloxy groups. And as the halogen of X in formula (II), included are say chlorine, bromine and iodine, and as M there are such groups as sodium, potassium, ammonium, triethylammonium and piperidinium groups.

Specific examples of the thiolcarbamate compounds of formula (I) that can be produced by the process of the instant invention include the following compounds.

1. α,α-dimethylbenzyl-N,N-diethylthiocarbamate
2. α,α-dimethylbenzyl-N,N-di-n-propylthiolcarbamate
3. α,α-dimethylbenzyl-N,N-di-i-propylthiolcarbamate
4. α,α-dimethylbenzyl-N,N-diallylthiolcarbamate
5. α,α-dimethylbenzyl-N-methyl-N-n-butylthiolcarbamate
6. α,α-dimethylbenzyl-N-methyl-N-allylthiolcarbamte
7. N-(α,α-dimethylbenzylthio-carbonyl)pyrrolidine
8. N-(α,α-dimethylbenzylthio-carbonyl)piperidine
9. N-(α,α-dimethylbenzylthio-carbonyl)hexamethyleneimine
10. N-(α,α-dimethylbenzylthio-carbonyl)-2-methylpiperidine
11. N-(α,α-dimethylbenzylthio-carbonyl)-3-methylpiperidine
12. N-(α,α-dimethylbenzylthio-carbonyl)-4-methylpiperidine
13. N-(α,α-dimethylbenzylthio-carbonyl)-2,4-dimethylpiperidine
14. N-(α,α-4-trimethylbenzylthio-carbonyl)hexamethyleneimine
15. N-(α,α-dimethyl-4-methoxybenzylthio-carbonyl)-hexamethyleneimine
16. N-(α,α-dimethyl-4-chlorobenzylthio-carbonyl)-hexamethyleneimine, and
17. N-(α,α-dimethyl-4-nitrobenzylthio-carbonyl)hexamethyleneimine the following examples will serve to illustrate the modes of practicing the present invention. It is to be understood however that the invention is to be in no way limited to these examples.

Preparation of N-(sodiumthio-carbonyl)hexamethyleneimine

A 100-ml round-bottom flask fitted with a magnetic stirrer, a gas blowing-in tube whose distal end fully reaches the lower part of the flask, and a gas discharge outlet was charged with 26 ml of water, 9.9 g (0.1 mole) of hexamethyleneimine and 4.0 g (0.1 mole) of sodium hydroxide. To the resulting solution was then introduced with stirring 7.2 g (0.12 mole) of carbonyl sulfide over the coarse of one hour via the gas blowing-in tube while cooling the mixture with ice. After completion of the introduction of all of the carbonyl sulfide, nitrogen was bubbled in for 30 minutes to eliminate any carbonyl sulfide remaining unreacted in the solution thereby obtaining 40 ml (0.1 mole) of an aqueous N-(sodiumthio-carbonyl)hexamethyleneimine solution.

EXAMPLES 1-5 and Comparative Examples 1-2

α,α-Dimethylbenzyl chloride [46.4 g (0.3 mole)] was added dropwise to 40 ml (0.1 mole) of an aqueous N-(sodiumthio-carbonyl)hexamethyleneimine solution while maintaining the pH value of the reaction mixture at 50° C. at the prescribed value indicated in Table 1 below by adding sodium hydroxide incrementally in small quantities. This was followed by carrying out the reaction for 2 hours at room temperature with stirring. After separating the organic and aqueous layers, the aqueous layer was extracted with 25 ml of hexane. The organic layers were then combined, and this hexane solution was quantitatively analyzed by means of the internal standard method gas chromatography (column: silicon OV 101 2% on gaschrom. Q glass column 4 mm φ×2 m. The results obtained are shown in Table 1 below.

TABLE 1

| Example or Comparative Example | pH | I Yield | II Yield | III Yield |
|---|---|---|---|---|
| Comp. Ex. 1 | 7–8 | 58.5 | 52.0 | 35.0 |
| Example 1 | 9.5–10 | 72.3 | 48.6 | 26.8 |
| Example 2 | 10–10.5 | 74.6 | 47.5 | 21.6 |
| Example 3 | 11–11.5 | 78.8 | 49.4 | 26.6 |
| Example 4 | 11.5–12.5 | 72.0 | 49.1 | 26.7 |
| Example 5 | 11–11.5 | 86.8 | 51.1 | 26.7 |
| Comp. Ex. 2 | 13.5–13.7 | 20.0 | — | — |

Note.-
In the table, I denotes N-(α,α-dimethylbenzylthiocarbonyl)hexamethyleneimine, and the yeild is based on thiolcarbamic acid salt; and II and III stand for α,α-dimethylbenzyl alcohol and α-methylstyrene, respectively, and the yields are based on α,α-dimethylbenzyl chloride.
In Example 4, (1.9 g (0.4 mole) of α,α-dimethylbenzyl chloride was reacted.

EXAMPLES 6-8

An aqueous N-(sodiumthio-carbonyl)hexamethyleneimine solution [40 ml (0.1 mole)], while maintaining its pH at about 10 to about 11 by adding sodium hydroxide incrementally in small quantities, was reacted as in Example 1 with 46.4 g (0.3 mole) of α,α-dimethylbenzyl chloride at the temperature indicated in Table 2 below. The reaction product was then quantitatively analyzed by means of gas chromatography. The results obtained are shown in Table 2.

TABLE 2

| Example | Reaction Temperature (°C.) | I (mole ) | II (mole %) | III (mole %) |
|---|---|---|---|---|
| 6 | 30 | 71.7 | 50.3 | 17.1 |
| 7 | 50 | 78.8 | 49.4 | 26.6 |
| 8 | 70 | 69.9 | 41.4 | 28.4 |

In the table, I, II and III have the same meanings as indicated hereinbefore.

When the reaction product of Example 7 shown in Table 2 was distilled under reduced pressure, 26.6 g of a mixture of α-methylstyrene and α,α-dimethylbenzyl alcohol was obtained as an initial fraction, and in the residue there was obtained 22.7 g of the intended N-(α,α-dimethylbenzylthio-carbonyl)hexamethyleneimine (purity 94%). This initial fraction mixture 26.6 g (0.20 mole) was stirred with [42.6 g (0.41 mole)] of conc. hydrochloric acid at room temperature for 3 hours. On separation of the organic layer from the reaction mixture, there was obtained 30.5 g of α,α-dimethylbenzyl chloride in a yield of 98.7%.

EXAMPLE 9

The α,α-dimethylbenzyl chloride [30.5 g (0.198) mole] recovered in Example 7 was added dropwise over the course of about one hour to 26.4 ml (0.066 mole) of an aqueous N-(sodiumthio-carbonyl)hexamethyleneimine solution while maintaining the pH of the reaction mixture at about 10 to about 11 by adding sodium hydroxide incrementally in small quantities and the temperature of the reaction mixture at 50° C. This was followed by stirring the reaction mixture for a further 2 hours at the same temperature to complete the reaction. On analysis of the reaction product liquid, there was obtained 14.5 g of the intended product (I) in a yield of 79.2% based on thiolcarbamate. The yields of compounds (II) and (III) based on α,α-dimethylbenzyl chloride were 48.7% and 26.8%, respectively.

EXAMPLE 10

A 5-liter round-bottom 3-necked flask fitted with a magnetic stirrer, a gas blowing-in tube whose distal end reaches the lower part of the flask, and a gas discharge outlet was charged with 940 ml of water, 358.4 g (3.62 moles) of hexamethyleneimine and 144.8 g (3.62 moles) of sodium hydroxide. To the resulting solution was then introduced with stirring 217.3 g (3.62 moles) of carbonyl sulfide over the course of one hour via the gas blowing-in tube while cooling the mixture with ice.

To the aqueous thiolcarbamic acid salt solution thus obtained was added and dissolved 72.4 g (1.81 moles) of powdered sodium hydroxide at 50° C., following which 279.8 g (1.81 moles) of α,α-dimethylbenzyl chloride was added dropwise at the same temperature over the course of 30 minutes. After repeating this operation three times, 559.6 g (3.62 moles) of α,α-dimethylbenzyl chloride was further added dropwise over the course of 30 minutes followed by stirring the reaction mixture at 50° C. for 1.5 hours to complete the reaction. During the reaction the pH of the system was 13.2–10.5. The organic layer and aqueous layer were separated, and the aqueous layer was washed in water and dried over sodium sulfate, followed by filtering off the desiccant and distillation of the residue under reduced pressure to give 993 g of a mixture of α-methylstyrene and α,α-dimethylbenzyl alcohol. On analysis of the mixture by means of gas chromatography, the yields based on α,α-dimethylbenzyl chloride were 34.4% (441 g) in the case of α-methylstyrene and 37.4% (552 g) in the case of α,α-dimethylbenzyl alcohol. In the residue there was obtained 880 g of the intended N-(α,α-dimethylbenzylthio-carbonyl) hexamethyleneimine. It was confirmed by gas chromatography that the purity of this product was 98.2% and that the yield based on thiolcarbamic acid salt was 86%.

EXAMPLES 11–13

α,α-Dimethylbenzyl chloride (46.4 g (0.3 mole)) was added dropwise over the course of one hour to an aqueous solution of sodium thiolcarbamate (0.1 mole) of the foregoing general formula (III) wherein M is Na, and either $R^1$ and $R^2$ are both the group —$CH_2CH=CH_2$, $R^1$ and $R^2$ are both the group —$CH_2CH_2CH_3$, or $R^1$ is —$CH_2CH_2CH_2CH_3$ and $R^2$ is methyl, the addition being made while maintaining the pH of the reaction mixture at about 10 to about 11.5 by adding sodium hydroxide incrementally in small quantities and the temperature of the reaction mixture at 50° C. The reaction was carried out for a further 2 hours with stirring to synthesize the intended thiolcarbamate derivative. The product thus obtained was quantitatively analyzed by gas chromatography. The yields and properties of the intended products are shown in Table 3, below.

EXAMPLE 14 p-Methyl-α,α-dimethylbenzylchloride [50.6 g (0.3 mole)] was added dropwise over the course of one hour to 40 ml (0.1 mole) of an aqueous N-(sodiumthio-carbonyl) hexamethyleneimine solution while maintaining the pH of the reaction mixture at about 10 to about 11.5 by adding sodium hydroxide incrementally in small quantities and the temperature of the reaction mixture at 50° C. This was followed by carrying out the reaction for 2 hours with stirring to produce N-(p-methyl-α,α-dimethylbenzylthiocarbonyl)hexamethyleneimine. The product was quantitatively analyzed by gas chromatography. The boiling point of this product was 150°–160° C./1 mm, and its $nD_{20}$ was 1.5654. The yield based on thiolcarbamic acid salt was 78.8 mole%.

EXAMPLE 15

25% Aqueous ammonia [13.6 g (0.2 mole)] was added to an aqueous ammonium thiolcarbamate solution obtained from 13.6 g (0.2 mole) of 25% aqueous ammonia and 7.2 g (0.12 mole) of carbonyl sulfide, following which 46.7 g (0.3 mole) of α,α-dimethylbenzyl chloride was added dropwise to the solution at room temperature over the course of about one hour. The reaction was then carried out for 2 hours with stirring. The pH of the system during the reaction was 11.4 to 9.5. After completion of the reaction, the organic layer and the aqueous layer were separated, following which the organic layer was wahsed with water and dried over sodium sulfate. After filtering off the desiccant, the residue was distilled under reduced pressure. The resulting crystallized residue was then washed in hexane to give 14.6 g of the intended product. The yield was 74.8%, and its melting point was 82.0–82.2° C.

EXAMPLES 16–17

Sodium hydroxide was added in a prescribed amount to 40 ml (0.1 mole) of an aqueous N-(sodiumthio-carbonyl) hexamethyleneimine solution. The reaction was then carried out by adding dropwise to this solution α,α-dimethylbenzyl chloride in a prescribed amount over the course of about one hour while maintaining the reaction temperature at 50° C. The product was then recovered as in Example 1 and quantitatively analyzed by gas chromatography. The pH of the reaction system was as shown in Table 4. The results obtained are also shown in Table 4.

TABLE 4

| Example | α,α-Dimethyl-benzyl chloride (mole) | NaOH (mole) | pH | I (mol %) | II (mole %) | III (mol %) |
|---|---|---|---|---|---|---|
| 16 | 0.30 | 0.20 | 12.5 | 71.4 | 41.7 | 33.1 |
| 17 | 0.40 | 0.30 | 13–10 | 70.0 | 42.0 | 40.6 |

In the talbe, I, II, and III have the same meanings as indicated hereinbefore.

TABLE 3

| | Thiolcarbamate derivative | | Yield (mol %) | | | Boiling point | Refractive index |
|---|---|---|---|---|---|---|---|
| Example | $R^1$ | $R^2$ | I | II | III | (°C./1 mm) | ($nD_{20}$) |
| 11 | —$CH_2CH=CH_2$ | —$CH_2CH=CH_2$ | 78.6 | 40.0 | 22.4 | 142–6 | 1.5561 |
| 12 | —$CH_2CH_2CH_3$ | —$CH_2CH_2CH_3$ | 75.4 | 45.7 | 28.5 | 132–5 | 1.5286 |
| 13 | —$CH_2CH_2CH_2CH_3$ | —$CH_3$ | 79.6 | 48.1 | 25.3 | 154–7 | 1.5451 |

In the table, I is the yield in each case of the intended thiolcarbamate derivative based on thiolcarbamic acid salt
II and III have the same meanings as indicated hereinbefore.

EXAMPLE 18

Preparation of a sample of N-(α,α-dimethylbenzylthiocarbonyl)piperidine

Water (120 l), piperidine (38.0 kg (447 moles)) and sodium hydroxide (18.8 g (447 moles)) were added and dissolved in a 500-liter glass-lined autoclave equipped with a stirrer, a gas feed inlet and a gas discharge outlet. Carbonyl sulfide (26.8 g (447 moles)) was then introduced from the gas inlet over the course of about 4 hours while stirring the reaction mixture at a temperature of below 20° C.

To the so obtained aqueous thiolcarbamic acid salt solution was added 7.2 kg (179 moles) of 40% sodium hydroxide at 50° to 60° C., following which 27.6 kg (179 moles) of α,α-dimethylbenzyl chloride was added dropwise at the same temperature over the course of 20 minutes. After repeating this operation four times, a further addition dropwise of 69.0 kg (447 moles) of α,α-dimethylbenzyl chloride was made over the course of 30 minutes. The reaction mixture was then stirred at 50° to 60° C. for 1.5 hours to complete the reaction. The pH of the system ranged from 9.5 to 12.5 during the reaction. After cooling the reaction mixture, 80 liters of hexane was added, and the organic layer and the aqueous layer were separated. The organic layer was then washed with 80 liters of 2% hydrochloric acid and 80 liters of water. After distilling the hexane off from this hexane solution, a 0.5 liter ethanol solution of 0.5 kg of p-toluenesulfonic acid was added, and the mixture was reacted and distilled under reduced pressure (10 to 20 mm Hg) at below 110° C. The intended N-(α,α-dimethylbenzylthio-carbonyl)piperidine (93 kg) was obtained in the residue. On analysis by gas chromatography, this product was found to have a purity of 96.0%, and its yield based on thiolcarbamic acid salt was 78.5%. The melting point was 34.5°–36.0° C.

We claim:

1. A process for the production of a thiolcarbamate compound of the formula

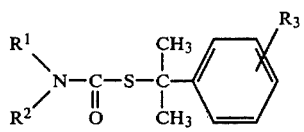 (I)

wherein $R^1$ and $R^2$, which may be the same or different, each represent a member selected from the group consisting of hydrogen, alkyl groups and alkenyl groups, and $R^3$ represents a member selected from the group consisting of hydrogen, halogen, nitro, alkyl groups and alkoxy groups, in which $R^1$ and $R^2$ taken together with N in the formula may form a hetero ring of the formula

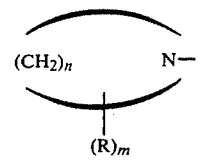

where R is hydrogen or an alkyl group of 1 to 4 carbon atoms, m is an integer from 1 to 2, and n is an integer from 2 to 6, said process comprising reacting a tertiary halogen compound of the formula

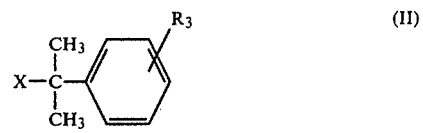 (II)

wherein X represents halogen, and $R^3$ is as defined above, with a thiolcarbamic acid salt of the formula

 (III)

wherein M represents a member selected from the group consisting of the alkali metals, ammonium group and immonium group, in an aqueous reaction medium, in the presence of a strong base; wherein the reaction is carried out under conditions in which the reaction system is adjusted to a pH ranging from about 9 to about 13.

2. The process as defined in claim 1 wherein the pH is about 9.5 to about 12.5.

3. The process as defined in claim 1 wherein said strong base is a member selected from the group consisting of sodium hydroxide, potassium, hydroxide and ammonia.

4. The process as defined in claim 1 wherein said strong base is used in an amount of about 0.1 to about 1.6 moles per mole of the compound of formula (II).

5. The process as defined in claim 1 wherein said compound of formula (II) is used in an amount of about 0.8 to about 6 equivalents based on said compound of formula (III).

6. The process as defined in claim 1 wherein the temperature of said reaction ranges from about 0° to about 100° C.

7. The process as defined in claim 1 which comprises adding said strong base incrementally or continuously to the reaction system to adjust the pH of the system.

* * * * *